(12) United States Patent  
Warnke et al.

(10) Patent No.: US 8,450,686 B1  
(45) Date of Patent: May 28, 2013

(54) SYSTEM AND METHOD FOR ANALYZING THERMAL IMAGES

(75) Inventors: Stefan Warnke, Santa Cruz, CA (US); James T. Pickett, Santa Cruz, CA (US)

(73) Assignee: Fluke Corporation, Everett, WA (US)

( * ) Notice: Subject to any disclaimer, the term of this patent is extended or adjusted under 35 U.S.C. 154(b) by 0 days.

(21) Appl. No.: 13/595,736

(22) Filed: Aug. 27, 2012

Related U.S. Application Data

(63) Continuation of application No. 12/186,134, filed on Aug. 5, 2008, now Pat. No. 8,253,105, which is a continuation-in-part of application No. 11/812,227, filed on Jun. 15, 2007.

(51) Int. Cl.
*G06K 9/60* (2006.01)

(52) U.S. Cl.
USPC .................. 250/330; 250/338.1; 382/305

(58) Field of Classification Search
USPC ........... 250/252.1, 330, 338.1, 339.04, 358.1; 382/305
See application file for complete search history.

(56) References Cited

U.S. PATENT DOCUMENTS 7,304,297 B1 * 12/2007 King et al. ................. 250/252.1

* cited by examiner

*Primary Examiner* — Mark R Gaworecki
(74) *Attorney, Agent, or Firm* — Nelson, Mullins, Riley & Scarborough LLP

(57) ABSTRACT

A thermal imaging system to facilitate analysis of thermal images comprises a portable thermal imager having a communication interface for transfer of data. The imager also has an on-board memory in which image data for corresponding thermal images is stored. A remote computer is operative to communicate with the thermal imager via the communication interface for download of the image data. The computer runs software operative to superimpose at least one marker at a selected location on a thermal image, the marker being saved on the image.

20 Claims, 11 Drawing Sheets

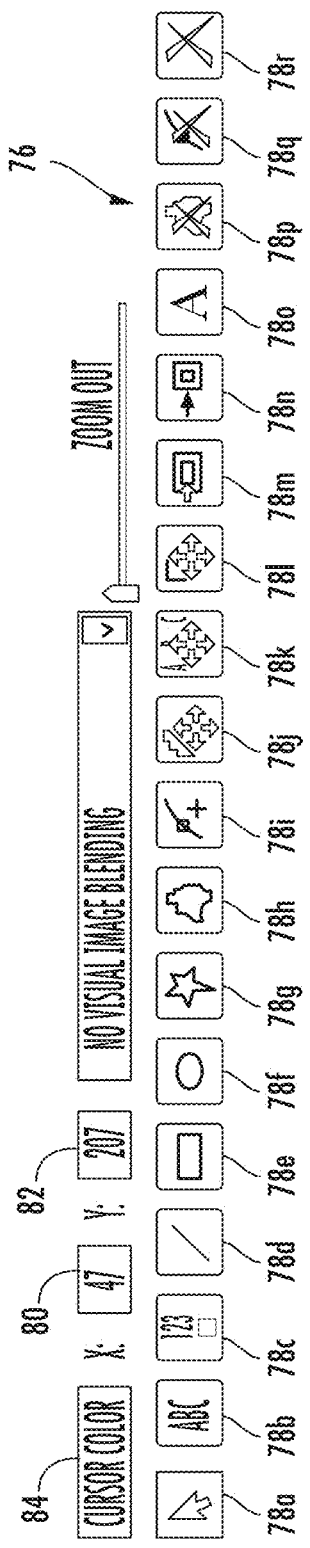

SYSTEM AND METHOD FOR ANALYZING THERMAL IMAGES

This application is a continuation of copending application Ser. No. 12/186,134, filed Aug. 5, 2008, which was a continuation-in-part (CIP) of application Ser. No. 11/812,227, filed Jun. 15, 2007.

BACKGROUND OF THE INVENTION

The present invention relates generally to the analysis of thermal images captured using a thermal imaging camera.

Thermal imaging cameras are used in a wide variety of applications, such as predictive maintenance in industrial facilities. Such cameras, often simply referred to as "thermal imagers," include some type of infrared engine that converts infrared energy into electrical signals. For example, many thermal imagers include a detector array located in the focal plane of the camera optics. Infrared energy impinging the focal plane array (FPA) is read out for further processing on a pixel-by-pixel basis.

The "raw" data produced by the infrared engine is then converted through digital signal processing techniques to the visible image that can be displayed. In this regard, objects in the image are often depicted in colors corresponding to their relative temperature. The processed images thus produced may be stored in the camera's local memory before subsequent download to a personal computer, such as using a serial data link.

Software running on the personal computer can then be used to organize the images. For example, different groups of equipment can be inspected and data specific to different plant areas or departments can be individually named, saved, stored and retrieved. The images can be stored as collections of images in a particular subfolder or can be organized as sequential images in a particular inspection route.

SUMMARY OF THE INVENTION

According to one aspect, the present invention provides a thermal imaging system to facilitate analysis of thermal images. The system comprises a portable thermal imager having a communication interface for transfer of data. The imager also has an on-board memory in which image data for corresponding thermal images is stored. A remote computer is operative to communicate with the thermal imager via the communication interface for download of the image data. The computer runs software operative to superimpose at least one marker at a selected location on a thermal image, the marker being saved on the image.

Preferably, emissivity of an image location corresponding to the marker is changeable by the user. In addition, the software may create marker text for the marker on the thermal image. The marker text may include a marker name changeable by the user. Moreover, the software may allow the marker text to be moved to a new location on the image without changing the selected location of the marker. Preferably, the marker text may include a displayed temperature. For example, the marker text may include minimum temperature, maximum temperature and an average temperature within the marker.

In preferred embodiments, the software is operative to allow a user to alter or delete the marker. Various forms of marker are contemplated, such as text marker, point marker, line marker, or a closed marker encompassing a marker area of the image (such as a polygonal marker or a closed curve marker). In the case of a closed marker, changing the emissivity of the marker area may thereby change a displayed color gradient in the marker area.

Preferably, images taken captured during multiple traversals of an inspection route may be stored by the software in the same order. In this regard, the software may be operative to populate the marker in corresponding images in the multiple traversals. Moreover, the software may preferably be operative to display a temperature trend occurring at the marker in the multiple traversals.

Another aspect of the present invention provides a computer-implemented method of analyzing a thermal image captured by a thermal imaging camera. One step of the method involves storing the thermal image in a memory of a computer device. The thermal image is also displayed on a display of the computer device. According to another step of the method, software running on the computer device is capable of superimposing a marker at a selected location on the thermal image as directed by a user. The software is further capable of allowing emissivity of the selected location to be changed by the user thereby changing a temperature at the selected location.

A further aspect of the present invention provides a thermal imaging system to facilitate analysis of thermal images. The system comprises a portable thermal imager having a communication interface for transfer of data. The imager has an on-board memory in which image data for corresponding thermal images is stored. A remote computer is operative to communicate with the thermal imager via the communication interface for download of the image data. The computer runs software operative to superimpose at least one marker at a selected location on a thermal image. The software is further capable of allowing emissivity of the selected location to be changed by the user thereby changing a temperature at the selected location.

An additional aspect of the present invention is achieved by a thermal imaging system to facilitate analysis of thermal images. The system comprises a portable thermal imager having a communication interface for transfer of data. The imager has an on-board memory in which image data for corresponding thermal images is stored. A remote computer is operative to communicate with the thermal imager via the communication interface for download of the image data. The computer runs software operative to store for display in the same order images captured during multiple traversals of an inspection route. The software is further operative to superimpose at least one marker at a selected location on a thermal image and to populate the marker in corresponding images in the multiple traversals.

According to an additional aspect, the present invention provides a data processing apparatus comprising a processor and a storage media containing at least one digital file corresponding to a thermal image. The storage media further has instructions being run on the processor to superimpose at least one marker at a selected location on the thermal image. The instructions are further capable of allowing emissivity of the selected location to be changed by a user thereby changing a temperature at the selected location. A display for showing the thermal image with the marker superimposed thereon is also provided.

Other objects, features and aspects of the present invention are provided by various combinations and subcombinations of the disclosed elements, as well as methods of practicing same, which are discussed in greater detail below.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying drawings, in which:

FIG. 9 is an enlarged view of the marker toolbar and adjacent features seen in the image screen display;

FIGS. 10A and 10B show the marker label portion of the image screen display to demonstrate the manner in which emissivity within a marker area can be changed;

Figure 1:
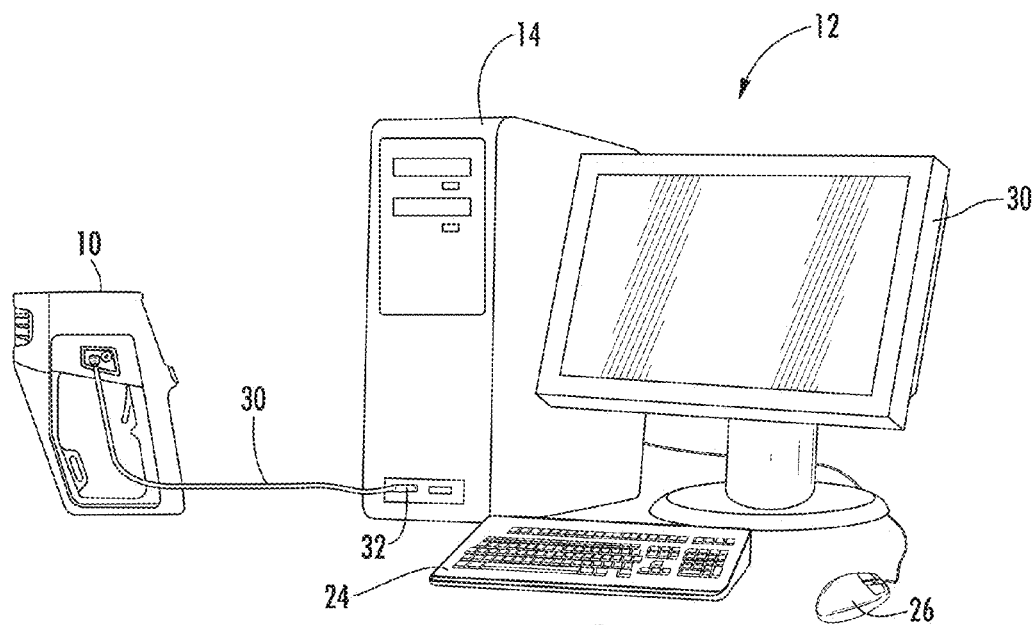
FIG. 1 shows a thermal imager in serial communication with a personal computer.

Repeat use of reference characters in the present specification and drawings is intended to represent same or analogous features or elements of the invention.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary constructions.

Referring now to FIG. 1, a thermal imager 10 is in electrical communication with a personal computer 12. As will be described more fully below, personal computer 12 has software that allows enhanced analysis of the downloaded images. It should be understood that the term "computer" as used herein is not limited to a traditional desktop or laptop personal computer. Instead, "computer" is included to cover other devices, such as various personal digital assistants (PDAs), that now or in the future may be capable of performing the described functionality.

Figure 2:
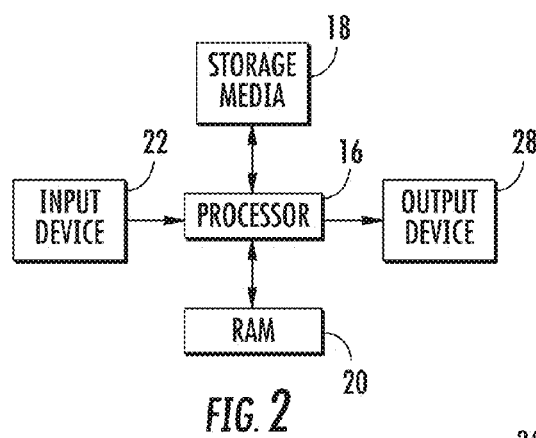
FIG. 2 is a diagrammatic representation showing various functional components of the personal computer of FIG. 1.

This embodiment utilizes a traditional desktop personal computer having a main housing 14 containing processing electronics, internal memory, disk drives and the like. Referring now also to FIG. 2, computer 12 in this embodiment has a processor 16 in operative communication with a storage media 18 and a random access memory (RAM) 20. One or more input devices 22 (such as a keyboard 24 and mouse 26 shown in FIG. 1) provides information to processor 16. Information is supplied to a user at output device 28, such as a suitable computer display 30 (FIG. 1). In this case the display is configured as an LCD that screen display.

The invention contemplates various techniques for providing a data link between imager 10 and computer 12, such as various wireless communication protocols. In the illustrated embodiment, however, electrical communication between imager 10 and computer 12 is accomplished using a typical serial cable 30. Cable 30 includes universal serial bus (USB) connectors at each end, one of which plugs into a corresponding port on the front of housing 14 (as indicated at 32).

Figure 3:
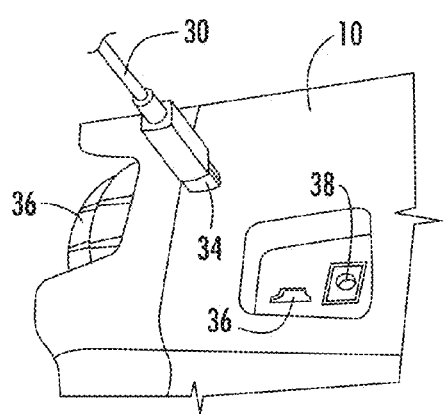
FIG. 3 is an enlarged view showing the USB connector port of the thermal imager shown in FIG. 1.

As can be most clearly seen in FIG. 3, the other connector 34 is configured in this example as a mini-USB connector. Connector 34 is inserted into a corresponding port 36 located on the side of imager 10. In this embodiment, a receptacle 38 is located adjacent to mini-USB port 36 for connecting a battery charger when necessary to recharge the imager's internal batteries.

Figure 5:
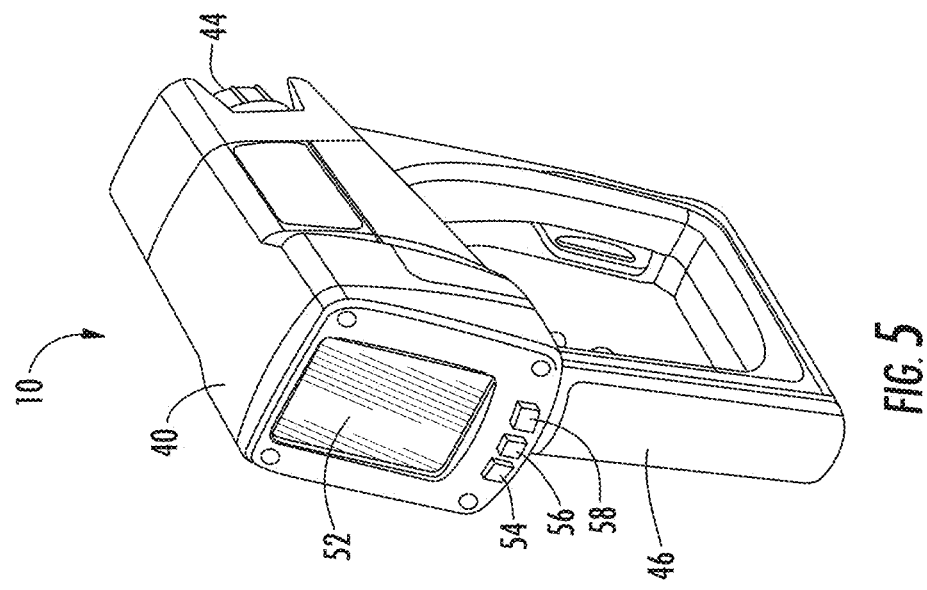
FIG. 5 is a rear perspective view of the thermal imager of FIG. 1.
Figure 4:
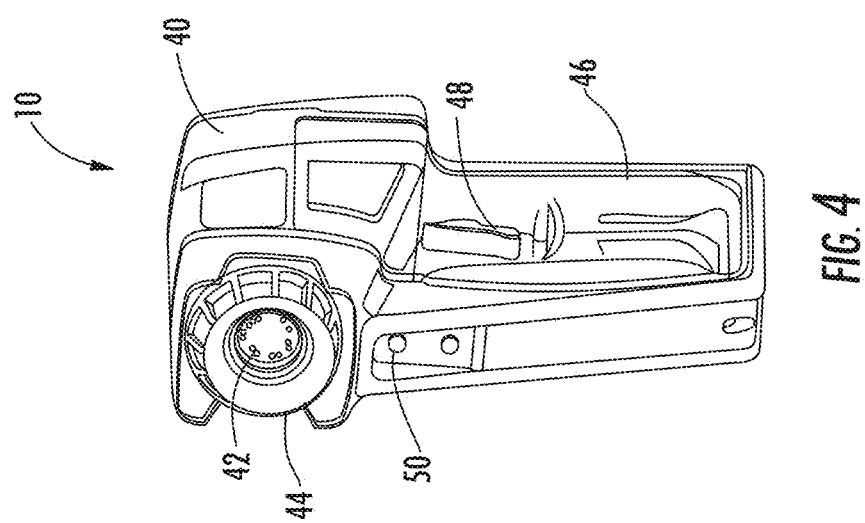
FIG. 4 is a front perspective view of the thermal imager of FIG. 1.

Referring now to FIGS. 4 and 5, certain details about the construction of imager 10 can be more easily explained. As shown, imager 10 includes a housing 40 in which the components of a thermal image camera are located. A lens 42 (FIG. 4) carried by a focus ring 44 is located near the front of housing 40. As one skilled in the art will appreciate, the target energy enters the device through this lens.

Housing 40 includes a handle 46 by which the operator holds and aims the device. A trigger 48 located on handle 46 permits the user to store selected images in the device's internal memory. In the illustrated embodiment, laser diode 50 (FIG. 4) projects a dot of light forward of the imager to facilitate aiming.

As shown in FIG. 5, a display 52 is preferably located at the rear of imager 10. In this case, the display is a color display of the LCD type. A plurality of function buttons 54, 56 and 58 are also located on the rear portion of housing 40. In this embodiment, buttons 54, 56 and 58 are used as "soft keys" to navigate the menu structure of the imager, access functions and select values for adjustable parameters. Button 56 is also used to turn the imager "on" and "off" (when pressed for a selected period of time, e.g., 2 seconds).

Referring again to FIG. 1, software on computer 12 may be used to download information to and upload information from thermal imager 10. For example, images that have been previously obtained through the use of imager 10 in the field can be read out of its internal memory into computer 12. Once the data is located in computer 12, it can be permanently stored, or used in the creation of maintenance reports and the like.

Figure 6:
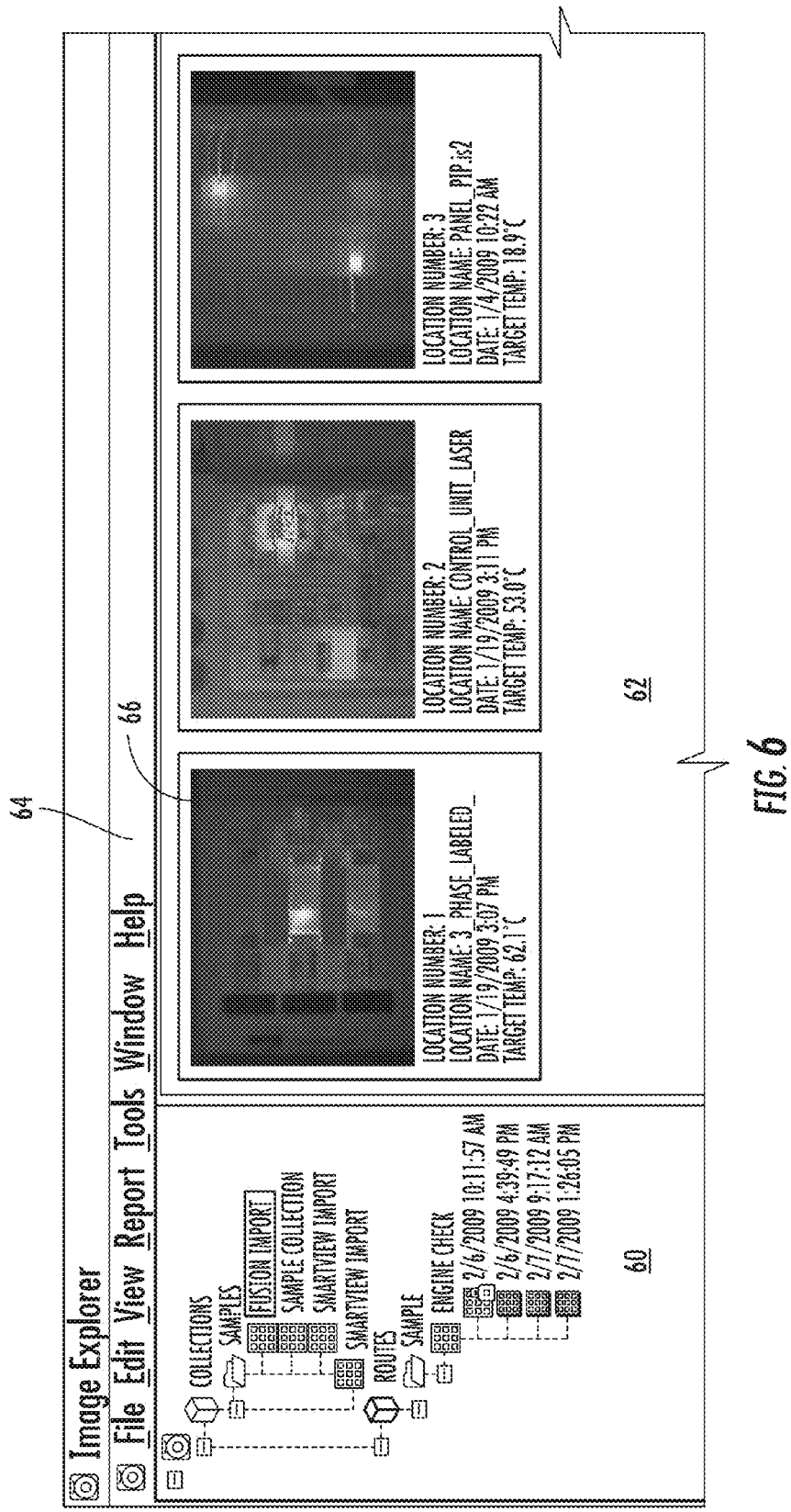
FIG. 6 shows a portion of an explorer screen display produced by software that may be run on the personal computer of FIG. 1 in accordance with the present invention.
Figure 7:
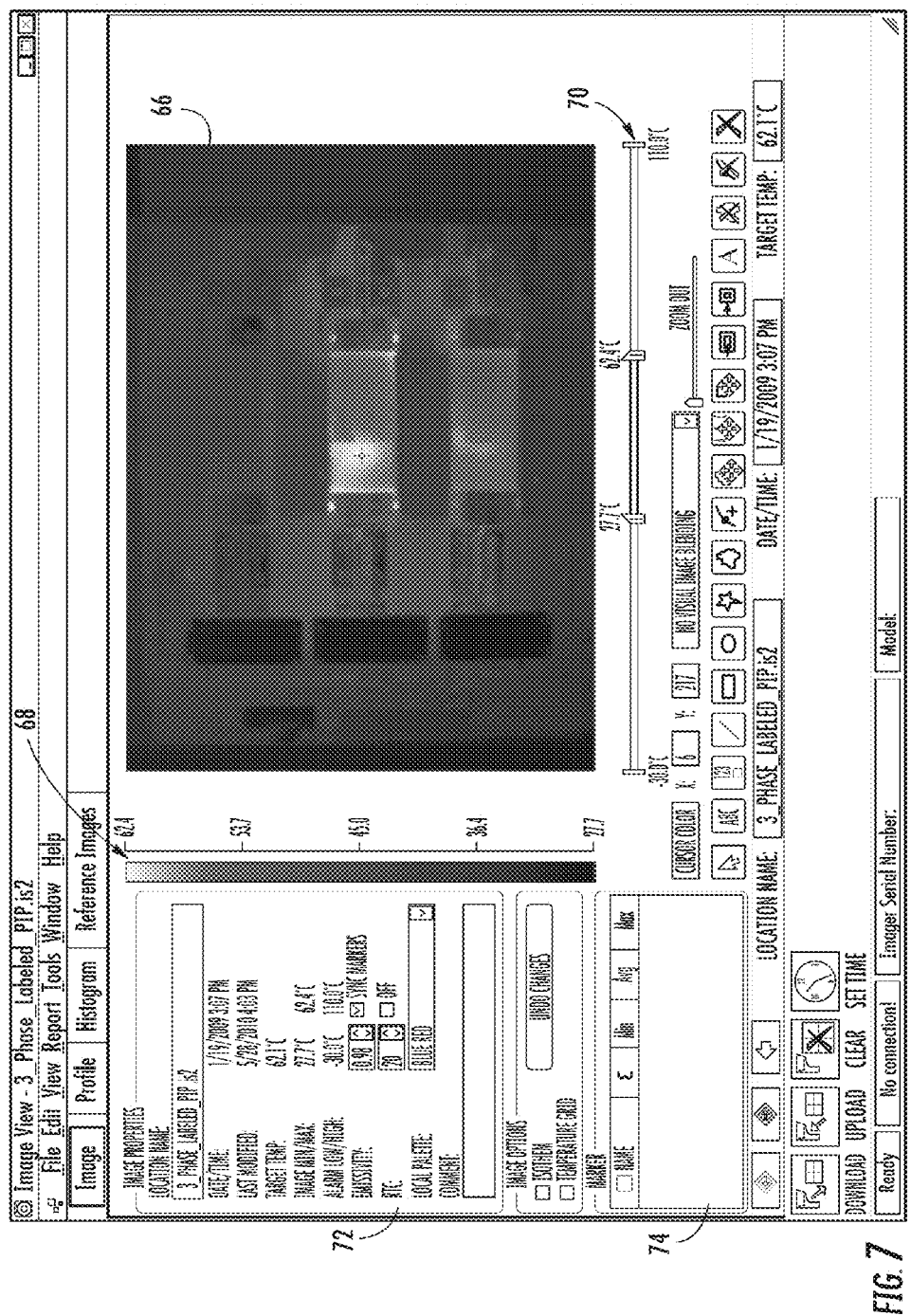
FIG. 7 shows an image screen display produced by the software.

In exemplary embodiments, the software may be configured to have two main views respectively illustrated in FIGS. 6 and 7. Referring now to FIG. 6, the "explorer view" has two primary portions 60 and 62 located below a menu bar 64. Menu bar 64 has commands File, Edit, View, Report, Tools, Window and Help corresponding to respective pull-down menus. Portion 60 is used to display folders labeled "Collections" and "Routes" and their respective subfolders. As one skilled in the art will appreciate, subfolders may be added by a user as necessary or desired. Portion 62 shows thumbnails of images (such as image 66) located in the selected subfolder.

The Collections folder is used to store a one time collection of images in a respective subfolder. Thus, clicking on a subfolder (such as Fusion Import) will display thumbnails of the images located in that subfolder. Textual information about the image will also be shown.

Subfolders under the Routes folder are established to contain image sets for scheduled inspections. In other words, it may be desired to traverse a particular inspection route on a periodic basis (such as daily) and capture thermal images of the same item in the same order. In this example, an inspection labeled "Engine Check" is being performed several times a day. The first subfolder, which contains the template for the route, is typically locked, but can be unlocked if changes to the route template are desired.

Double clicking on a particular image, such as image 66, will cause the age view shown in FIG. 7 to be displayed. As a result, image 66 will be enlarged to be more easily seen by the user. In this view, a vertical gradient scale is located just to the left of enlarged image 66 (as indicated at 68). Gradient scale 68 shows the assigned colors that correspond to temperatures at various pixels in the image. In this case, for example, the minimum temperature in the image is 27.7° C. whereas the highest temperature in the image is 62.4° C. The software chooses the gradient scale which most effectively displays the temperature variations. A horizontal slider 70 located below enlarged image 66 depicts the difference between the maximum and minimum temperatures in the image as a portion of a larger temperature scale.

Selection of the tab labeled "Image" displays an image properties area 72. This area provides information about the image, such as the date and time on which the image was captured. Other information can be changed as desired, such as the file name for the image as well as the emissivity and RTC (reflective temperature compensation) values used to determine temperatures at various points in the image. Immediately below the image properties area 72 is a marker label portion 74.

Figure 8:
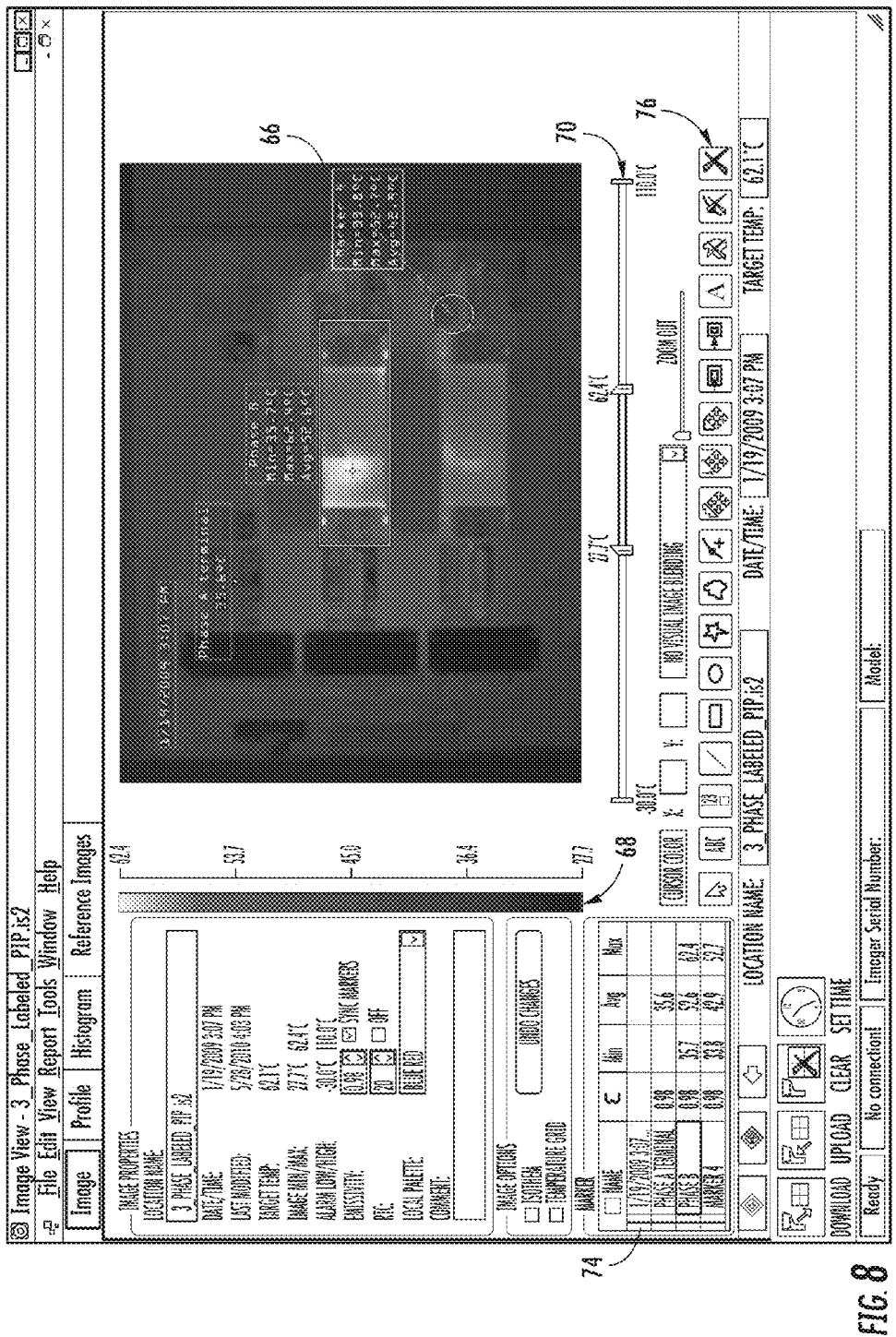
FIG. 8 is a view similar to FIG. 7 but showing various markers superimposed over the image.

Referring now to FIG. 8, the software permits the user to apply various markers over the image for the purpose of analysis. Via an easy to use and intuitive user interface, the operator can superimpose the markers directly over the infrared image such as by picking a tool from a selection in a tool bar or button with icons. Basic geometrical shapes such as point, line, rectangle, ellipse, polygon or closed curve by multiple points based on spline algorithm can be used. Preferably, the marker or its text block can be easily moved by the user. Single points can be inserted or deleted, complete markers can be deleted and color, outline color or fonts can be changed using the mouse. Selectable line and outline colors make the lines and text more visible on colorful temperature images as background. While the markers are superimposed on the image, they do not alter the underlying image data. Thus, when markers are deleted, the integrity of the underlying image data is preserved.

In this case, for example, a total of four markers have been superimposed on image 66. The first marker is simply a time stamp, which can be located anywhere on the image, indicating that the image was captured on Jan. 19, 2009 at 3:07 PM. The second marker is a point marker indicating the temperature (35.6° C.) at a single pixel in the image. When initially applied, the marker will have its default name "Marker 2." This has been changed to "Phase A Terminal" by the user in marker label portion 74. In particular, the user simply double clicks on the name in marker label portion 74 to activate the rename function. Once renamed, the name of the marker will change in both marker label portion 74 and the image marker itself.

The third marker, named Phase B, is a rectangle drawn around a particular area in the image. Similarly, Marker 4 (which has not yet been renamed) is a circle located around a selected area of the image. The creation of a marker enclosing an area of the image creates adjacent marker text typically showing the minimum, maximum and average temperature of the enclosed area. Portions of the text block may be enabled or disabled by the user, as desired. If the marker text appears in an inconvenient location, it may be moved by the user. For example, the text block corresponding to Marker 4 has been moved, with an umbilical line extending from the text block to the center of the marker area to indicate the connection between both.

The marker functions are selected by a tool bar 76, which may be located below enlarged image 66 as shown. Referring now to FIG. 9, tool bar 76 includes a total of eighteen buttons 78a-r corresponding to different marker functions that can be selected. Preferably, each of the buttons will contain a graphical icon indicative of its function. The selected button, in this case button 78a, may be outlined in bold for the user's convenience.

Button 78a activates the cursor tool (which, in a preferred embodiment, may be active by default when an image opens). As the cursor is moved across an image, the temperature value assigned to the particular pixel over which the cursor then appears will be displayed. The X and Y text boxes 80 and 82 located above tool bar 76 will indicate the present cursor position. Cursor color may be changed at 84 to make it more noticeable against the background color.

Clicking button 78b enables the text marking/time stamp tool. In a preferred embodiment, activation of this tool will produce a cursor shaped like a pencil. The pencil is then pointed at a location on the image where the time stamp is desired. Clicking at this location will thus produce the time stamp (e.g., Marker 1 described above). The time stamp can be changed to any label desired by choosing the corresponding "Name" in marker label portion 74 and changing the time stamp to some other text.

Button 78k is the move marker text tool. Activating this tool, the lines of text corresponding to a marker can be changed to a different location in the image. As noted above, the marker text will preferably be connected to its corresponding marker by an umbilical, at least when the marker text is selected by a user.

Buttons 78m and 78n may be used to change the marker text and text outline colors, respectively. Button 78o allows the font of marker text to be changed as desired.

Button 78c is the point marker tool. This button allows the creation of a point marker such as the marker named "Phase A Terminal" in FIG. 8.

Figure 12:
FIG. 12 is a portion of an image showing a line marker and adjacent text.

Referring now also to FIG. 12, activation of button 78d enables the line marker tool. When this feature is activated, the cursor is first positioned at a point on the image where the line marker should begin. The user clicks and drags the cursor to draw a line in the image. When the line is applied to the image, marker text containing the minimum, maximum and average temperatures that cover the pixels beneath the line is also created. While a straight line marker is shown in this example, various arcs and other lines are contemplated within the scope of the present invention.

Buttons 78e and 78f respectively activate rectangle and ellipse marker buttons. A marker using these features is formed by first moving the marker over the image to a desired starting location. The user then clicks and drags to form the remainder of the marker. When the click is released, marker text appears at a location adjacent to the marker thus formed.

Figure 13:
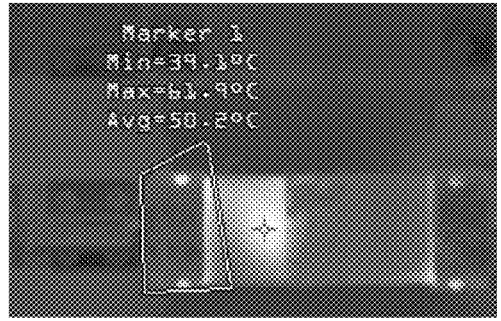
FIG. 13 is a portion of an image showing a polygonal marker and adjacent text.
Figure 15:
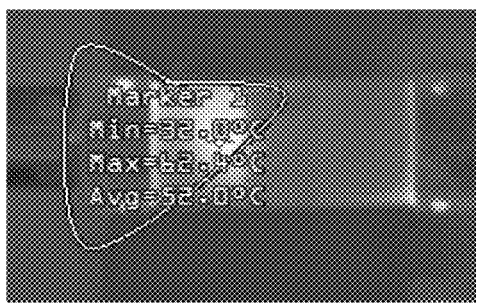
FIG. 15 is a portion of an image showing a closed curve marker and adjacent text.

Buttons 78g and 78h respectively activate the polygon and closed curve markers. These features allow the user to create a marker of indeterminate shape on a point-by-point basis. For example, FIG. 13 illustrates a marker created using the polygon marker feature 78g by positioning four points at various locations on the image. Similarly, FIG. 15 illustrates a marker created using closed curve marker feature 78h by inserting four points on the image at desired locations.

With the same number of points, the marker shape can be edited using the marker edit tool 78l. The entire marker can be moved to a new location by activation of the move marker tool 78j.

Figure 14:
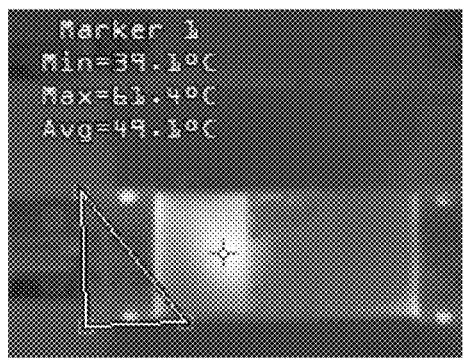
FIG. 14 shows the polygonal marker of FIG. 13 after deletion of a point.
Figure 16:
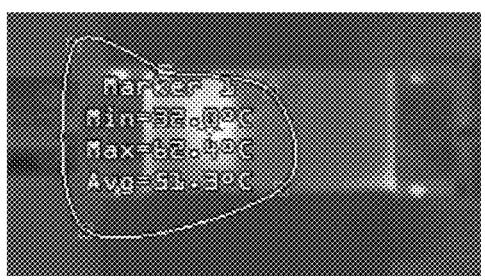
FIG. 16 shows the closed curve marker of FIG. 15 after addition of a point.

Individual points can be deleted using the delete point feature 78q. This is shown in FIG. 14, where the four-sided marker of FIG. 13 has been converted to a more triangular shape by deletion of a single point. Points can also be added to the marker using the insert point feature 78i. This is shown in FIG. 16, where a fifth point has been added to the marker of FIG. 15.

Feature 78p can be utilized to delete a single marker from the image. The feature represented by button 78r deletes all markers from the image.

Figure 11:
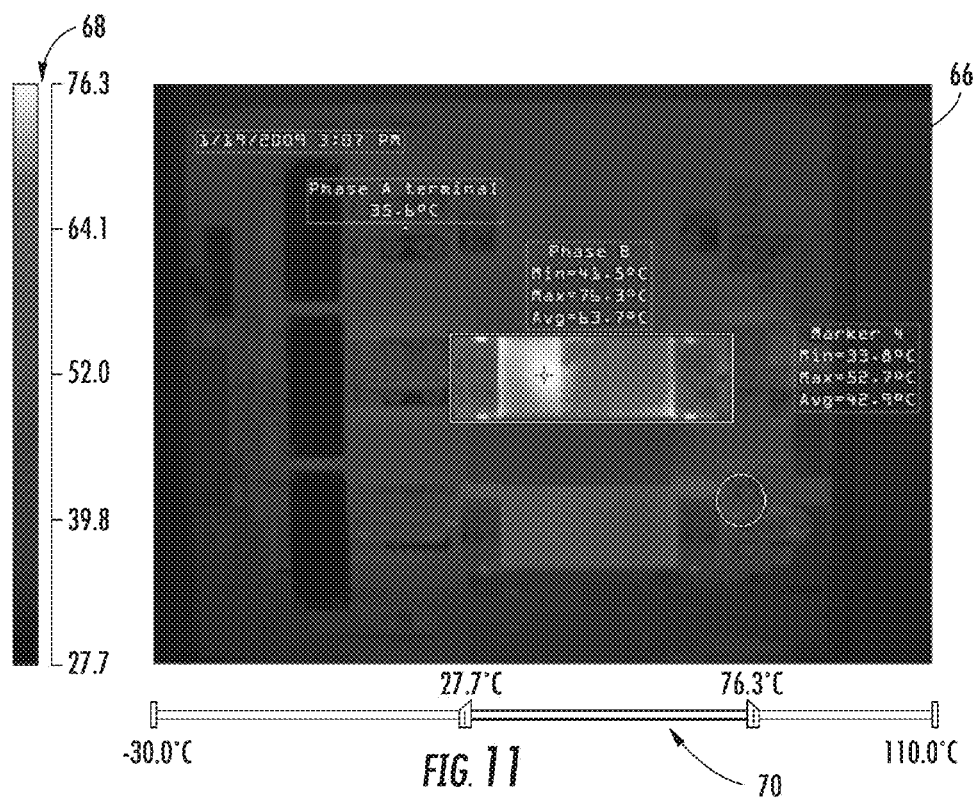
FIG. 11 shows an enlarged view of the thermal image after emissivity within a marker area has been changed.

According to an aspect of the present invention, the emissivity of the image can be changed within a marker without affecting the emissivity of surrounding areas. For example, if the object shown inside of a particular marker has a known emissivity, the emissivity of the marker can be changed accordingly. This is illustrated in FIGS. 10A and 10B, where the user knows that the emissivity of the Phase B marker (Marker 3) should 0.70 rather than 0.98. Thus, by selecting the emissivity of the Phase B marker in marker label portion 74, the emissivity can be changed as desired. This results in an automatic revision of the minimum, maximum and average temperatures shown by the corresponding marker text. In addition, as shown in FIG. 11, the slider 70 changes to reflect the new temperature scale of image 66.

Figure 17:
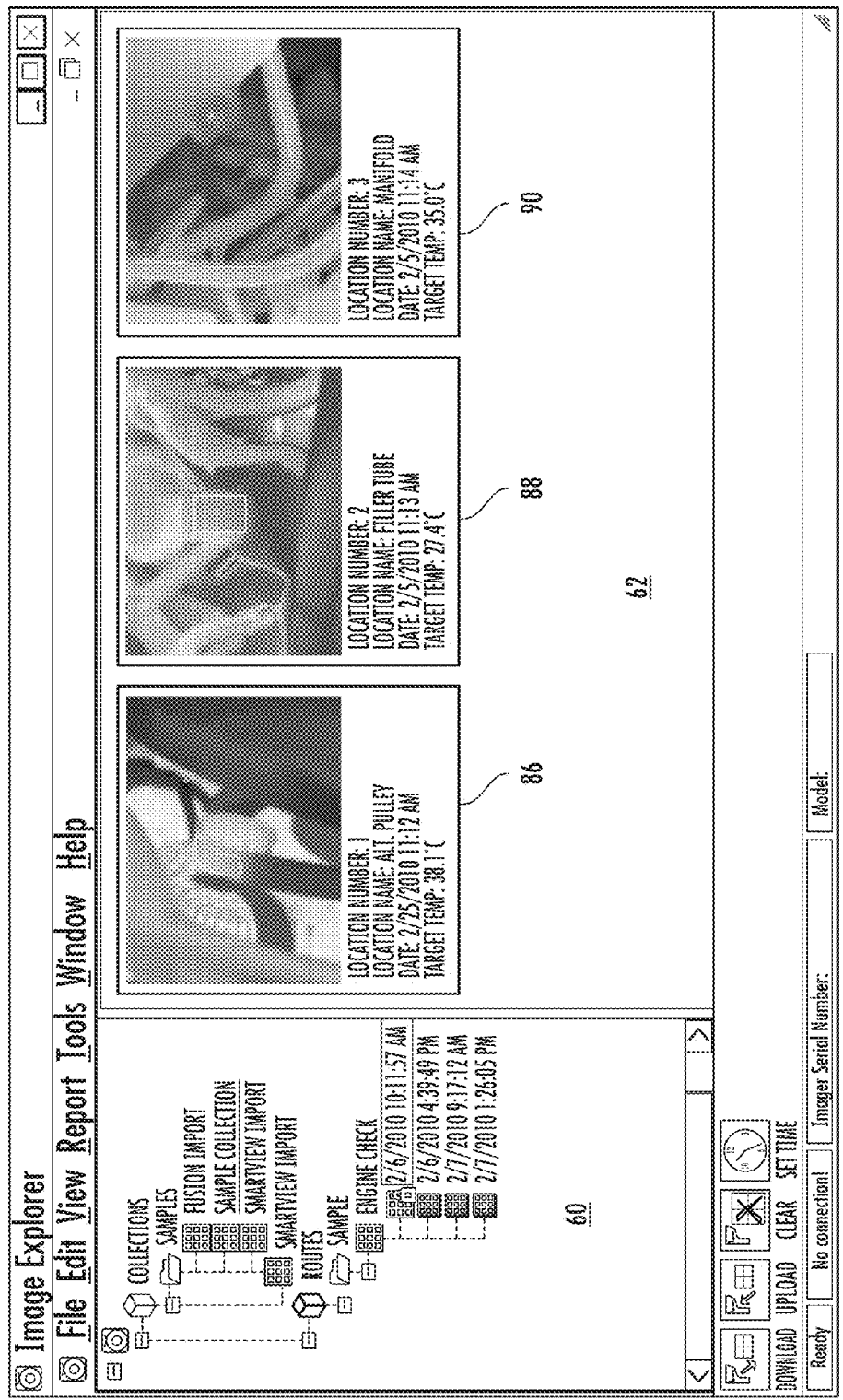
FIG. 17 shows the explorer view with a route selected.

FIG. 17 shows an "explorer" view in which a route template has been selected in display portion 60 to show thumbnails 86, 88 and 90 of the route images. In this case, the route images correspond to inspections of an engine alternator pulley, filler tube and manifold.

Figure 18:
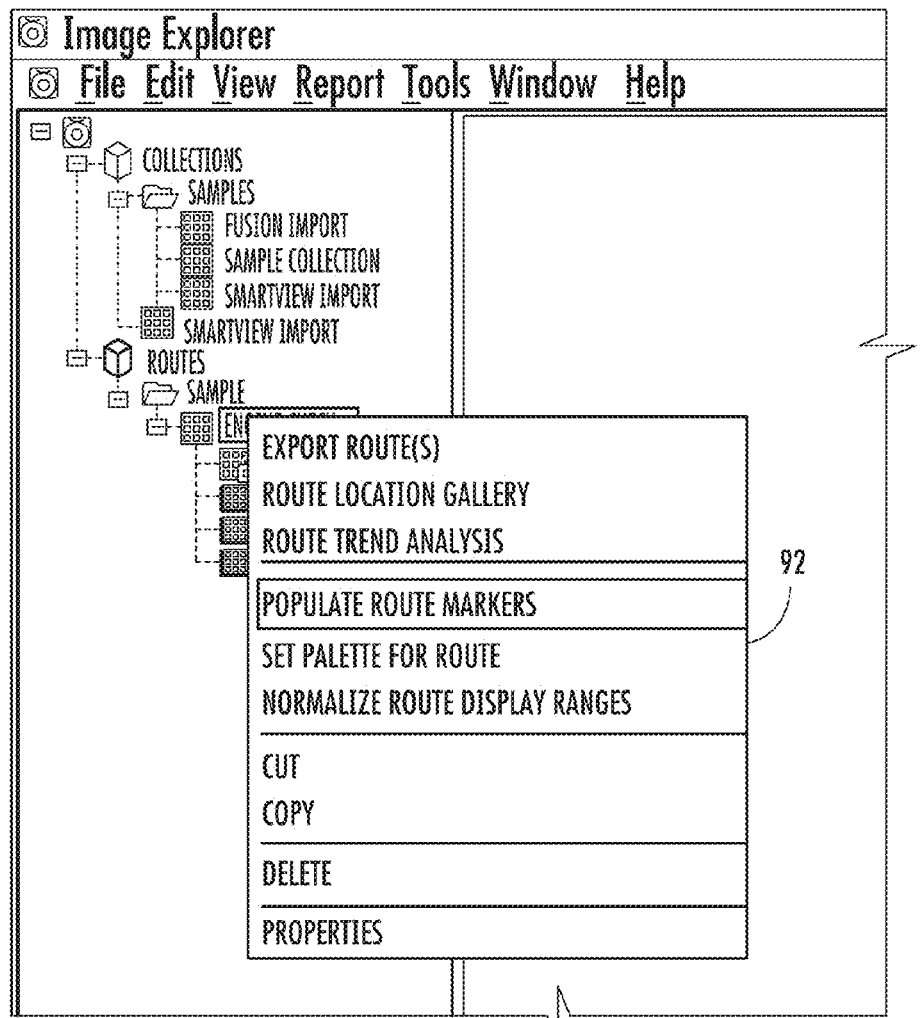
FIGS. 18 and 19 show windows that may be used to populate route markers on images captured during subsequent traversals of a route.
Figure 19:
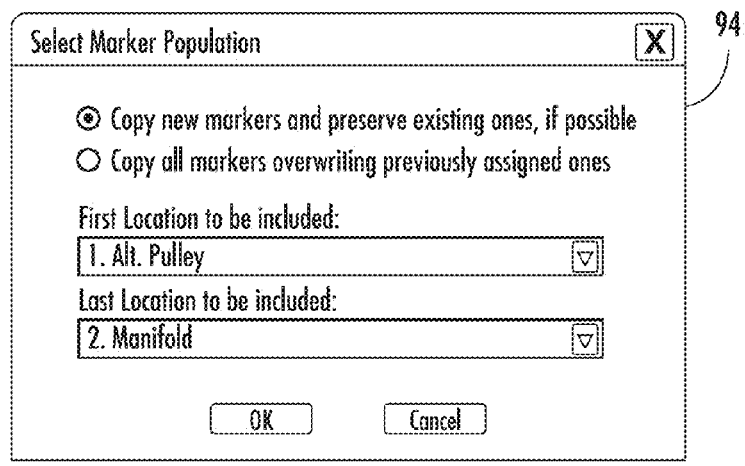

Referring now to FIGS. 18 and 19, an aspect of the present invention allows all route inspections under the template to be populated with all markers from corresponding images. In the illustrated embodiment, this is accomplished by selecting the subfolder corresponding to the particular route and right clicking to open menu 92. Selection of the item "Populate Route Markers" opens the Select Marker Population window 94 (FIG. 19). This window allows the user to copy new markers while preserving existing ones or overriding old ones. The first and last locations within the route to be included can also be selected.

Figure 20:
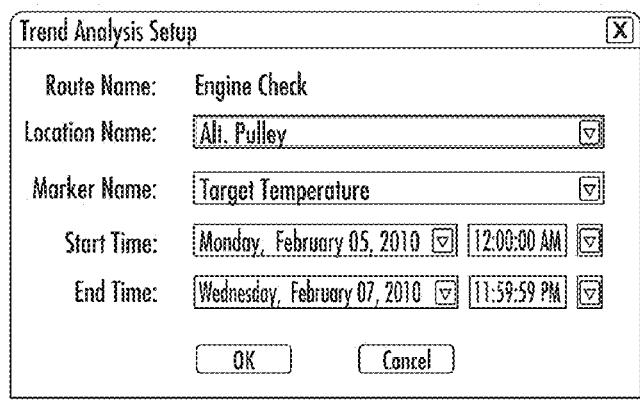
FIG. 20 shows a window that may be used to produce a trend analysis for a particular marker in corresponding route images.

Referring to FIG. 20, the illustrated embodiment of the present invention also allows the user to retrieve and plot the temperature of a common marker within a series of images from a particular route to show the marker's temperature trend over time. This is achieved from menu 92 by selecting the item "Route Trend Analysis." A window 96 will thus appear allowing the user to choose a location and marker for which the trend analysis is to be performed.

Figure 21:
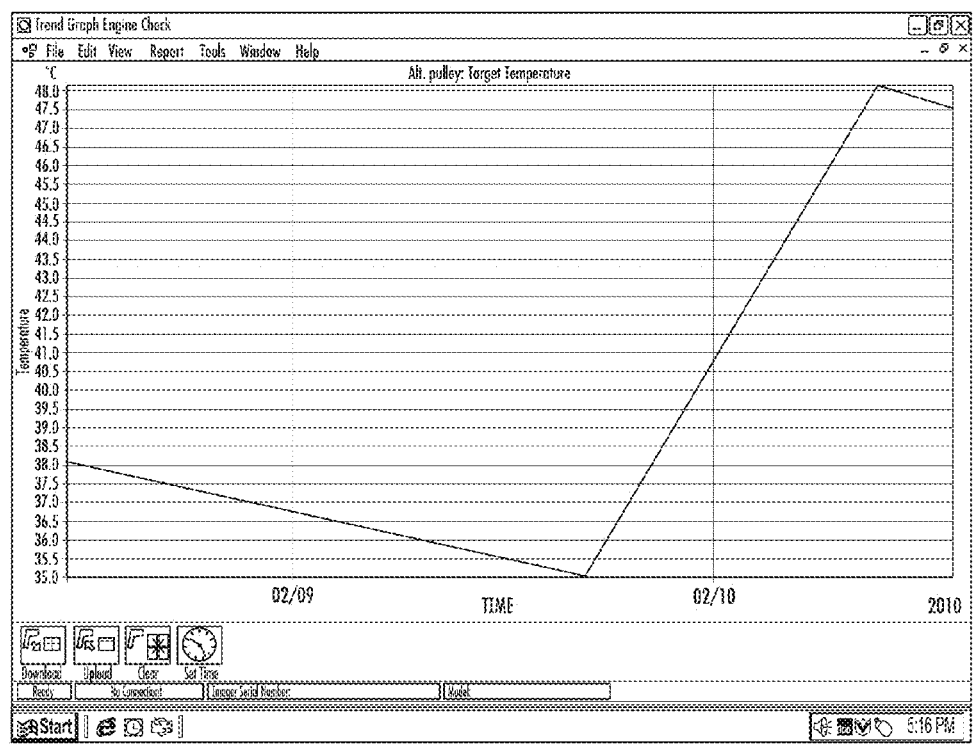
FIG. 21 shows a trend graph for a particular marker in corresponding route images.

After the appropriate selections are made, a trend graph as show FIG. 21 will then appear. This type of trend analysis can be included in reports that can be created by the operator using various report features included in the software.

It can thus be seen that the present invention provides a novel system and method for analyzing thermal images. While preferred embodiments of the invention have been shown and described, modifications and variations may be made thereto by those of ordinary skill in the an without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to be limitative of the invention as further described in the appended claims.

What is claimed is:

1. A data processing apparatus comprising:
    wireless communication circuitry;
    a storage media;
    a processor in operative communication with said wireless communication circuitry and said storage media;
    a flat screen display; and
    said storage media having instructions being run on said processor to perform the following:
        (a) receive a digital file corresponding to a thermal image via said wireless communication circuitry and store said digital file at said storage media;
        (b) retrieve said digital file from said storage media and show said thermal image on said display as part of a user interface; and
        (c) superimpose at least one marker at a selected location on said thermal image as directed by a user.

2. A data processing apparatus as set forth in claim 1, wherein said instructions being run on said processor are further operative to store for display in the same order images captured during multiple traversals of an inspection route and to populate said marker in corresponding images in said multiple traversals.

3. A data processing apparatus as set forth in claim 1, wherein said instructions are further capable of allowing emissivity of said selected location to be changed by a user thereby changing a temperature at said selected location.

4. A data processing apparatus as set forth in claim 1, wherein said instructions are operative to superimpose a plurality of markers on said thermal image.

5. A data processing system as set forth in claim 1, wherein said instructions are operative to create marker text for said marker on said thermal image.

6. A data processing system as set forth in claim 5, wherein said marker text includes a marker name changeable by a user.

7. A data processing system as set forth in claim 5, wherein said marker text can be moved to a new location on said thermal image without changing said selected location of said marker.

8. A data processing system as set forth in claim 5, wherein said marker text includes a displayed temperature.

9. A data processing system as set forth in claim 5, wherein said marker text includes minimum temperature, maximum temperature and an average temperature within said marker.

10. A data processing system as set forth in claim 1, wherein said marker is a point marker.

11. A data processing system as set forth in claim 1, wherein said marker is a line marker.

12. A data processing system as set forth in claim 1, wherein said marker is a closed marker encompassing a marker area of the image.

13. A data processing system as set forth in claim 12, wherein emissivity of said marker area is changeable by said user thereby changing a displayed temperature and thus color gradient in said marker area.

14. A data processing system as set forth in claim 13, wherein said closed marker is a polygonal marker.

15. A data processing system as set forth in claim 13, wherein said closed marker is a closed curve marker.

16. A thermal imaging system to facilitate analysis of thermal images, said system comprising:
- a portable thermal imager having a wireless communication interface for wireless transfer of data, said imager having an on-board memory in which image data for corresponding thermal images is stored; and
- a data processing apparatus located remote from portable thermal imager but capable of wireless communication with said portable thermal imager to receive data therefrom representative of at least one thermal image, said data processing device further comprising processing circuitry operative to show said thermal image on a display of said data processing device and superimpose at least one marker at a selected location on said thermal image as directed by a user.

17. A thermal imaging system as set forth in claim 16, wherein said data processing apparatus is further operative to store for display in the same order images captured during multiple traversals of an inspection route and to populate said marker in corresponding images in said multiple traversals.

18. A thermal imaging system as set forth in claim 16, wherein said data processing apparatus is further operative to allow emissivity of said selected location to be changed by a user thereby changing a temperature at said selected location.

19. A thermal imaging system as set forth in claim 16, wherein said data processing apparatus is operative to superimpose a plurality of markers on said thermal image.

20. A thermal imaging system as set forth in claim 16, wherein said said data processing apparatus is operative to create marker text for said marker on said thermal image.

* * * * *